United States Patent [19]
Askea et al.

[11] Patent Number: 5,458,002
[45] Date of Patent: Oct. 17, 1995

[54] VISCOELASTIC MATERIAL TESTING SYSTEM

[75] Inventors: Donald W. Askea, Akron; Jeffrey W. Johnson, North Lawrence, both of Ohio

[73] Assignee: The B. F. Goodrich Company, Akron, Ohio

[21] Appl. No.: 243,254

[22] Filed: May 16, 1994

[51] Int. Cl.⁶ .................................................. G01N 3/00
[52] U.S. Cl. .............................................. 73/789; 73/788
[58] Field of Search ........................... 73/789, 788, 795, 73/796, 826, 836

[56] References Cited

U.S. PATENT DOCUMENTS

| | | | |
|---|---|---|---|
| 2,886,967 | 5/1959 | Conti | 73/836 |
| 3,379,054 | 4/1968 | Folweiler | 73/789 |
| 3,699,808 | 10/1972 | Ford et al. | 73/789 |
| 3,969,930 | 7/1976 | Prevorsek et al. | 73/789 |
| 4,998,825 | 3/1991 | Hublikar et al. | 73/826 |

FOREIGN PATENT DOCUMENTS

| | | | |
|---|---|---|---|
| 0643623 | 3/1937 | Germany | 73/836 |
| 0781672 | 11/1980 | U.S.S.R. | 73/826 |
| 0021049 | 8/1912 | United Kingdom | 73/836 |

Primary Examiner—Hezron E. Williams
Assistant Examiner—Max H. Noori
Attorney, Agent, or Firm—Renner, Otto, Boisselle & Sklar

[57] ABSTRACT

A system for testing various properties of a viscoelastic material includes a balanced beam supporting an anvil upon which the material is placed, the balanced beam having a fixed state and a movable state, a load assembly for applying a static load to the material when the balanced beam is in a movable state and inducing an initial static strain on the material when the beam is in a fixed state, a hammer opposite the anvil for applying a dynamic strain to the material, a first sensor which senses the dynamic strain applied to the material by the hammer when the balanced beam is in the fixed state, a load cell which detects the force response of the material to the initial static strain and the dynamic strain when the balanced beam is in the fixed state, and a second sensor which senses permanent dimensional changes in the material when the balanced beam is in the movable state.

14 Claims, 2 Drawing Sheets 5,458,002

VISCOELASTIC MATERIAL TESTING SYSTEM

FIELD OF THE INVENTION

The invention relates generally to system and method for testing viscoelastic properties of a material, and, more particularly, to a system and method capable of performing flexometer tests on a material to determine temperature rise and permanent set and tests to determine certain fundamental viscoelastic properties of the material, such as the storage modulus and loss modulus.

BACKGROUND OF THE INVENTION

It is often desirable to characterize many of the properties of a specimen or compound to assist in predicting the response of the compound in various applications, to aid in research and development of compounds and as an aid in quality control of a manufactured compound. For example, it is desirable to be able to predict the rolling resistance that a vehicle tire made of a certain rubber compound would have without actually building and testing a tire made of that compound. This rolling resistance can be predicted or inferred from certain characteristics of a rubber sample, such as the temperature change and permanent set of a material when subjected to a flexometer test.

One type of flexometer, the Goodrich type flexometer, is described in Method A of ASTM Designation: D 623, entitled, "Standard Test Methods For Rubber Property—Heat Generation and Flexing Fatigue in Compression." Such a flexometer is relatively inexpensive and small, but provides only limited information on material characteristics, such as temperature change and permanent set. Other devices are available which are able to determine the fundamental viscoelastic properties of a specimen, but are often extremely expensive, large and complicated. Further, many of these machines do not perform flexometer type testing.

It would be desirable to provide a system for performing flexometer tests as well as other tests to determine the fundamental viscoelastic properties of a material which was relatively inexpensive, small and simple to operate.

SUMMARY OF THE INVENTION

The present invention provides a system and method for performing flexometer tests as well as other tests for determining viscoelastic properties of a material. The device is easily converted from a configuration for performing flexometer tests to one for performing tests for fundamental viscoelastic properties by locking a balanced beam member into place and informing a processor of the test to be performed.

In accordance with one aspect of the invention, a device for testing various properties of a viscoelastic material includes a balanced beam supporting an anvil upon which the material is placed, the balanced beam having a fixed state and a movable state, a load assembly for applying a static load to the material when said balanced beam is in a movable state and inducing an initial static strain on said material when said balanced beam is in a fixed state, a hammer opposite the anvil for applying a dynamic strain to the material, a first sensor which senses the dynamic strain applied to the material by the hammer when the balanced beam is in the fixed state, a load cell which detects the force response of the material to the initial static strain load and the dynamic strain when the balanced beam is in the fixed state, and a second sensor which senses permanent dimensional changes in the material when the balanced beam is in the movable state.

In accordance with another aspect of the invention, a device for testing various properties of a viscoelastic material includes a balanced beam supporting an anvil upon which the material is placed, the balanced beam having a fixed state and a movable state, a load assembly for applying a static load to the material when said balanced beam is in a movable state and inducing an initial static strain on said material when said balanced beam is in a fixed state, a hammer opposite the anvil for applying a dynamic strain to the material, a first sensor which senses the dynamic strain applied to the material by the hammer when the balanced beam is in a fixed state, a load cell which detects the force response of the material to the initial static strain and the dynamic strain when the balanced beam is in a fixed state, and a thermocouple which senses the temperature of the material when the balanced beam is in the movable state.

In accordance with a further aspect of the invention a method for testing various properties of a viscoelastic material includes the steps of selecting between a first test and a second test to be performed, applying a static load to the material when said second test is selected and inducing an initial static strain on said material when said first test is selected, applying a dynamic strain to the material, sensing the dynamic strain applied to the material when the first test is selected, detecting the force response of the material to the initial static strain and the dynamic strain when the first test is selected, and sensing permanent dimensional changes in the material when the second test is selected.

In accordance with a still further aspect of the invention a method for testing various properties of a viscoelastic material includes the steps of selecting between a first test and a second test to be performed, applying a static load to the material when said second test is selected and inducing an initial static strain on said material when said first test is selected, applying a dynamic strain to the material, sensing the dynamic strain applied to the material when the first test is selected, detecting the force response of the material to the initial static strain load and the dynamic strain when the first test is selected, and sensing the temperature of the material when the second test is selected.

The foregoing and other features of the invention are hereinafter fully described and particularly pointed out in the claims, the following description and the annexed drawings setting forth in detail certain illustrative embodiments of the invention, these being indicative, however, of but a few of the various ways in which the principles of the invention may be employed. It will be appreciated that the scope of the invention is to be determined by the claims and the equivalents thereof.

DETAILED DESCRIPTION OF THE INVENTION

Figure 1:
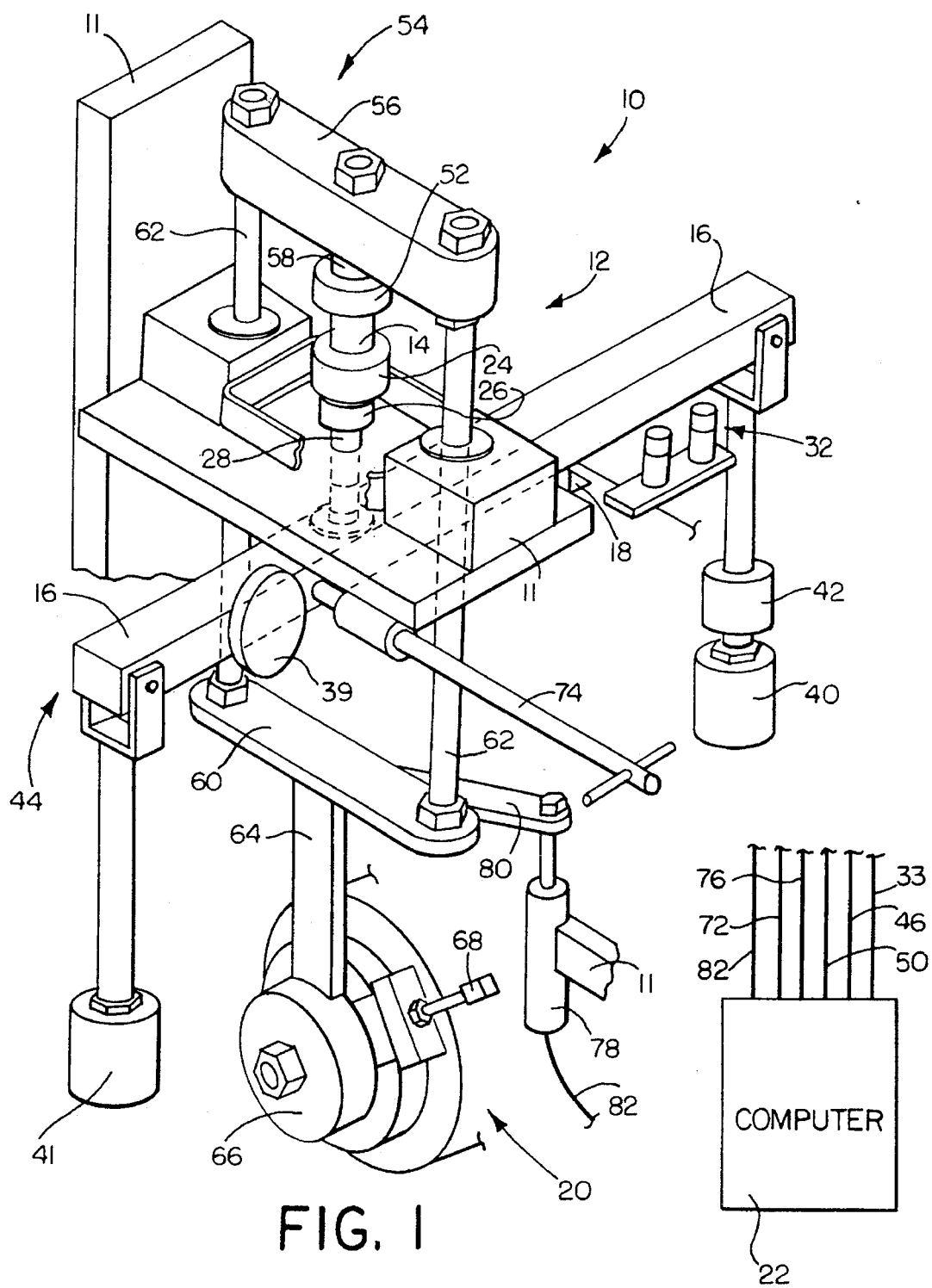
FIG. 1 is a partial isometric view of a test system in accordance with the present invention.

With reference to the drawings and initially to FIG. 1, there is shown a test system 10 in accordance with one embodiment of the present invention. The test system 10 preferably is operable in at least two modes, such as in a mode to perform a flexometer test and a mode to perform a test to determine certain fundamental viscoelastic properties of the test material, for example, the storage modulus, loss modulus and tan delta.

The test system 10 includes a frame 11, a test fixture 12 into which the test specimen 14 is placed, an oven (not shown) surrounding the test specimen and a portion of the test fixture, a high inertia balanced beam 16 balanced on the fulcrum 18, a drive system 20 and a computer 22. The computer 22 controls various aspects of the test, collects test data and computes desired properties of the test specimen 14 from the collected test data in accordance with the test which has been selected for operation. The computer may be any of a number of processing units and related components capable of interacting with remote devices, capable of obtaining and digitizing data and capable of performing the required computation of the data described below.

Figure 2:
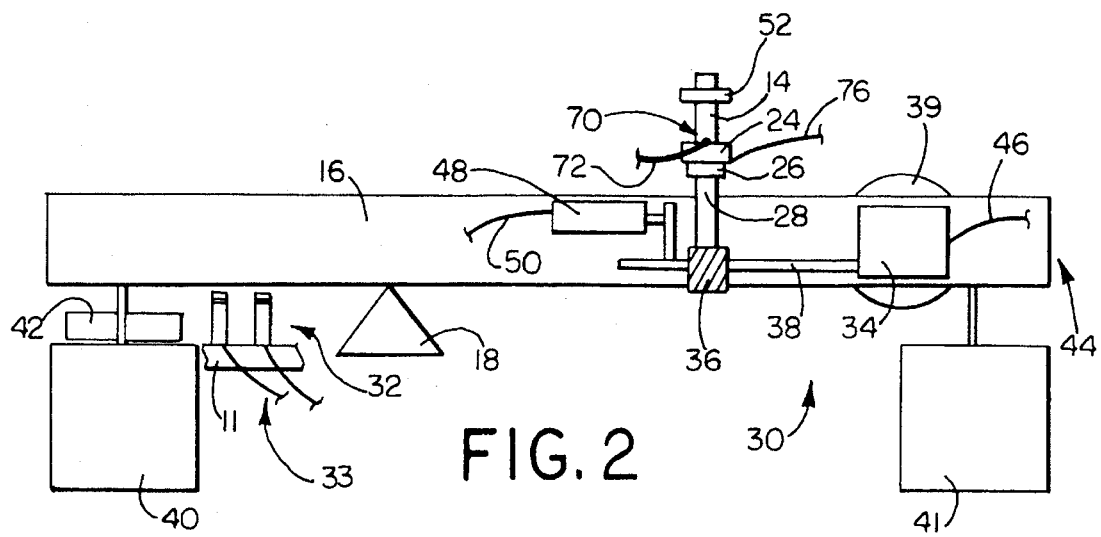
FIG. 2 is a partial side view of the test system of FIG. 1.

The lower portion of the test fixture 12 includes an anvil 24, upon which the test specimen 14 sits, connected to the balanced beam 16 through load cell 26, positional shaft 28, and leveling system 30 shown in FIG. 2. The leveling system 30 includes a pair of magnetic proximity sensors 32 connected to the computer 22 via lines 33 which in combination allow the computer to determine if the balanced beam 16 is level, a levelling motor 34, a drive gear 36 enmeshed with suitable gears on the positional shaft 28, and a drive shaft 38 connecting the levelling motor and drive gear. Rotation of drive shaft 38 by the leveling motor 34 thus causes the drive gear 36 to rotate. The rotation of the drive gear 36 is translated into vertical movement of the positional shaft 28 and anvil 24 through cooperation of the gears of the drive gear and the gears on the positional shaft. A manual leveling crank 39 is also provided which interfaces with the drive shaft 38 to raise or lower the anvil 24 in the same manner as is accomplished by the leveling motor 34.

At either end of the balanced beam 16 is suspended an inertial weight 40, 41 which in combination add inertia to the balanced beam so that it is not substantially effected by the relatively high frequency waveform felt by the anvil 24 during a flexometer test. A load weight 42 may be placed above the rear inertial weight 40 thereby causing a static force to be translated through the balanced beam 16, the positional shaft 28, load cell 26 and anvil 24 to act upon the test specimen 14. When the test system 10 is performing a flexometer test, as described in more detail below, most test specimens 14 will likely undergo a small permanent reduction in their height during the test. This phenomenon is known as "permanent set." A change in the permanent set of the test specimen 14 will cause the forward end 44 of the balanced beam 16 to tend to tip slightly toward the test specimen 14 by virtue of the static loading applied by the load weight 42. Any tipping of the balanced beam 16 is detected by the proximity sensors 32 and reported to the computer 22 which will command the leveling motor 34 via line 46 to rotate in the appropriate direction to raise or lower the positional shaft 28 and anvil 24 relative to the balanced beam. Since the anvil 24 is prevented from moving by the test specimen 14, the balanced beam 16 will adjust its position and thus be maintained level during a flexometer test.

A displacement transducer 48, such as a linear variable differential transformer (LVDT) senses any positional change in the positional shaft 28 and anvil 24 relative to the balanced beam 16. Any such positional changes sensed by the displacement transducer 48 are collected by the computer 22 via a connection 50 between the displacement transducer and the computer and are stored by the computer as changes in the permanent set of the test specimen 14.

The upper portion of the test fixture 12 includes a hammer 52, as is seen in FIG. 1, positioned above the anvil 24 and abutting the top of the test specimen 14, and a drive frame 54. The drive frame 54 includes an upper cross member 56 connected to the hammer 52 by rod 58, a lower cross member 60, and a pair of vertical posts 62 extending between upper and lower cross members. The posts 62 are vertically, slidably mounted to the frame 11, thus restricting the hammer 52 to vertical movement with the drive frame 54.

The lower cross member 60 of the drive frame 54 is connected to a tie rod 64 eccentrically mounted to the drive system 20 through adjustable disk 66. Rotation of drive system 20 thus causes a vertical cyclic stroke of the tie rod 64, drive frame 54 and hammer 52, the amplitude of which is determined by the degree of eccentricity of the connection between the tie rod and drive system. The degree of eccentricity and thus the amplitude of the stroke of the hammer 52 is adjustable through the adjustment bolt 68.

To perform a flexometer test with the test system 10, an operator will place a test specimen 14 of the viscoelastic material to be tested between the anvil 24 and hammer 52. The operator then adds the appropriate load weight 42 to the rear inertial weight 40, levels the balanced beam 16 using the leveling crank 39, sets the desired stroke of the hammer 52 through the adjustment bolt 68, and informs the computer 22 that a flexometer test is to be performed. Some test variables, such as the oven temperature, the frequency of the hammer stroke, and the test duration, may be set by entering the variables into the computer 22 or by adjusting them manually when the computer is not set up to control the test variable. When the test is commenced, the hammer 52 will cycle vertically thereby exerting a dynamic strain on the test sample 14 while the sample is concurrently subjected to a static load from the load weight 42. A thermocouple 70 (See FIG. 2), preferably mounted to the top of the anvil 24 and positioned below the test sample 14 senses the temperature of the test sample throughout the test and transfers the sensed temperature as an electrical signal to the computer 22 over the line 72 for storage as a function of time. Any adjustments made to level the balanced beam 16 during the test in response to changes in permanent set of the test sample 14 are sensed by the displacement transducer 48 and transferred to the computer 22 over the line 50.

Figure 3:
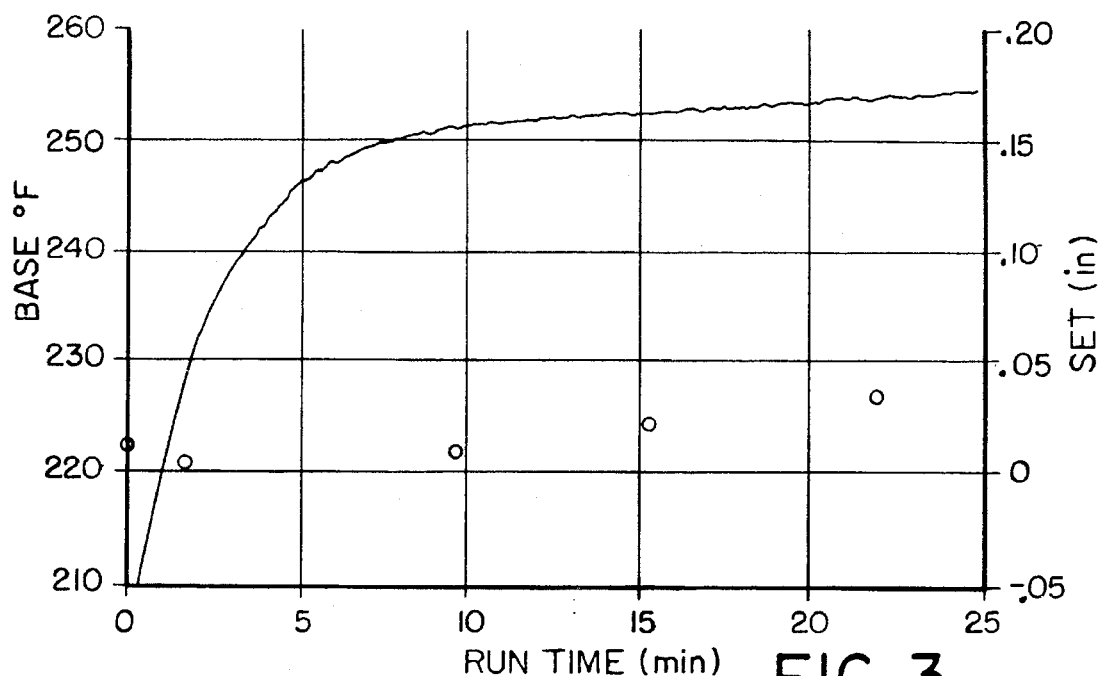
FIG. 3 is a graphical plot of temperature as a function of run time in minutes for a flexometer test.

Once the flexometer test is completed, typically after around 25 minutes, the operator can command the computer to print the results or to display or print a graphical plot of the desired test results, such as a plot of temperature and permanent set for the test sample 14 as a function of time as shown in FIG. 3.

When it is desired to perform a different test, such as a dynamic mechanical test to determine certain fundamental viscoelastic properties of a test specimen, the test system 10 is readily reconfigured to change testing capabilities. To perform a dynamic mechanical test (DMT), the operator slides pin 74, shown in FIG. 1, to engage the balanced beam 16. As the pin 74 is slidably mounted to the frame 11, the balanced beam is then supported at two points, the fulcrum 18 and the pin 74 and thus is fixed during the test. Since the balanced beam 16 is fixed, any desired initial static strain can be induced on the specimen 14 by rotating the leveling crank 39 (FIG. 2).

The operator then sets the desired stroke of the hammer 52 through the adjustment bolt 68, and informs the computer 22 that a dynamic mechanical test is to be performed. Some test variables, such as the oven temperature, the frequency of the hammer stroke, and the test duration, may be set by entering the variables into the computer 22 or by adjusting them manually when the computer is not set up to control the test variable.

Figure 4:
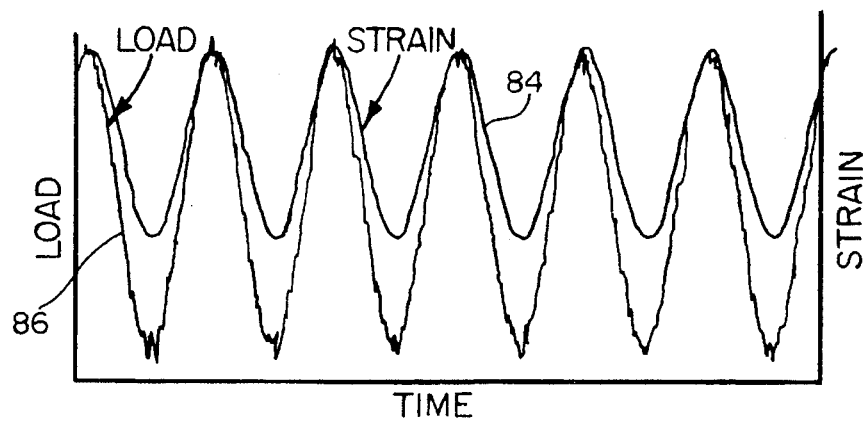
FIG. 4 is a superimposed plot of strain applied to a test specimen and the waveform of the force response of the specimen to the applied strain as a function of time.

When the test is commenced, the hammer 52 will cycle vertically thereby exerting a dynamic strain on the test sample 14 while the sample is concurrently subjected to a static load by the adjustment to the height of the anvil 24. During the test the computer 22 will sample the signal output by the load cell 26 over line 76 to develop a waveform of the force response of the test material 14 to the applied dynamic strain over time. As the drive system 20 rotates and drives the drive frame 54 and hammer 52 through their stroke, the position of the drive frame, and thus the position of the hammer, is sensed by the positional transducer 78 (See FIG. 1) connected between the frame 11 and an extension arm 80 of the drive frame 54. The positional transducer 78 may be a linear variable differential transformer or a similar device which develops an electrical signal as a function of linear position and transfers the signal to the computer 22 over line 82. During the test the output of the positional transducer 78 over the line 82 is sampled by the computer 22, which develops a waveform of the dynamic strain applied to the test specimen by correlating the sampled data with time. FIG. 4 illustrates the waveform 84 of the applied strain exerted by the hammer 52 on the test sample 14 and the force response waveform 86 of the test sample for an exemplary test.

At the conclusion of the test the computer 22 will calculate the phase shift or difference between the two waveforms using a suitable technique such as a Fast Fourier Transform algorithm. The complex modulus (E*) of the test sample can then be calculated and reduced to the storage modulus (E') and the loss modulus (E"), as well as to tan delta (E"/E') for the test sample through known methods.

What is claimed is:

1. A system for testing various properties of a viscoelastic material, comprising:
   a balanced beam supported by a fulcrum and supporting an anvil upon which said material is placed, said balanced beam having a fixed state and a movable state movable about said fulcrum;
   an assembly for applying a static load to said material when said balanced beam is in a movable state and inducing an initial static strain on said material when said beam is in a fixed state;
   a hammer opposite said anvil for applying a dynamic strain to said material;
   a first sensor which senses the dynamic strain applied to said material by said hammer when said balanced beam is in a fixed state;
   a load cell which detects the force response of said material to said initial static strain and said dynamic strain when said balanced beam is in a fixed state; and
   a second sensor which senses permanent dimensional changes in said material when said balanced beam is in said movable state.

2. The system of claim 1, further including a processor for determining the phase difference between the waveform of applied dynamic strain and the waveform of the force response of the material.

3. The system of claim 2, wherein said processor further calculates certain fundamental viscoelastic properties of the material from said phase difference, the waveform of the applied dynamic strain and the waveform of the force response of the material.

4. The system of claim 1, including a thermocouple which senses the temperature of said material when said balanced beam is in said movable state.

5. The system of claim 1, including a locking pin for locking the balanced beam into a fixed state.

6. The system of claim 1, wherein said hammer is cyclically moved by a eccentric connection to a drive motor.

7. The system of claim 1 further including a plurality of inertial weights disposed generally at opposite ends of said balanced beam.

8. The system of claim 1, including a leveling mechanism for leveling said balanced beam when the system is in said movable state.

9. A system for testing various properties of a viscoelastic material, comprising:
   a balanced beam supported by a fulcrum and supporting an anvil upon which said material is placed, said balanced beam having a fixed state and a movable state movable about said fulcrum;
   an assembly for applying a static load to said material when said balanced beam is in a movable state and inducing an initial static strain on said material when said beam is in a fixed state;
   a hammer opposite said anvil for applying a dynamic strain to said material when said balanced beam is in a movable state and inducing an initial static strain on said material when said beam is in a fixed state;
   a first sensor which senses the dynamic strain applied to said material by said hammer when said balanced beam is in said fixed state;
   a load cell which detects the force response of said material to said initial static strain and said dynamic strain when said balanced beam is in said fixed state; and,
   a thermocouple which senses the temperature of said material when said balanced beam is in said movable state.

10. The system of claim 9, including a second sensor which senses permanent dimensional changes in said material when said balanced beam is in said movable state.

11. The system of claim 9, wherein said thermocouple is mounted to said anvil.

12. The system of claim 10, wherein said first and second sensors are linear variable differential transformers.

13. The system of claim 9, further including a processor for determining the phase difference between the waveform of applied dynamic strain and the waveform of the force response of the material.

14. The system of claim 13, wherein said processor further calculates certain fundamental viscoelastic properties of the material from said phase difference, the waveform of the applied dynamic strain and the waveform of the force response of the material.

* * * * *